(12) United States Patent
Shinozaki et al.

(10) Patent No.: US 8,043,093 B2
(45) Date of Patent: Oct. 25, 2011

(54) DENTAL ROOT CANAL-FILLING COMPOSITION

(75) Inventors: Yutaka Shinozaki, Itabashi-ku (JP); Hiroshi Kamohara, Itabashi-ku (JP)

(73) Assignee: GC Corporation, Tokyo (JP)

( * ) Notice: Subject to any disclaimer, the term of this patent is extended or adjusted under 35 U.S.C. 154(b) by 107 days.

(21) Appl. No.: 12/560,917

(22) Filed: Sep. 16, 2009

(65) Prior Publication Data

US 2010/0081113 A1 Apr. 1, 2010

(30) Foreign Application Priority Data

Sep. 30, 2008 (JP) .................................. 2008-251990

(51) Int. Cl.
*A61C 5/50* (2006.01)

(52) U.S. Cl. ..................................... 433/228.1; 433/226

(58) Field of Classification Search ............... 433/228.1, 433/226; 106/35; 523/116
See application file for complete search history.

(56) References Cited

U.S. PATENT DOCUMENTS

| | | | |
|---|---|---|---|
| 4,740,245 A * | 4/1988 | Futami et al. ................... | 106/35 |
| 4,850,871 A * | 7/1989 | Bryan ........................... | 433/213 |
| 4,854,875 A * | 8/1989 | Dziki et al. .................... | 433/213 |
| 4,882,407 A * | 11/1989 | Riazi ............................ | 526/340.2 |
| 4,943,237 A * | 7/1990 | Bryan ........................... | 433/213 |
| 4,950,697 A * | 8/1990 | Chang et al. ................... | 523/116 |
| 5,437,875 A * | 8/1995 | Synosky et al. .................. | 426/3 |
| 5,646,197 A | 7/1997 | Martin | |
| 5,994,450 A * | 11/1999 | Pearce ........................... | 524/505 |
| 6,028,125 A * | 2/2000 | Combe et al. ................... | 523/116 |
| 6,220,863 B1 | 4/2001 | Kamohara et al. | |
| 6,387,392 B1 * | 5/2002 | Saito et al. ..................... | 424/435 |
| 6,568,937 B2 * | 5/2003 | Kamohara et al. .......... | 433/228.1 |
| 7,086,864 B2 * | 8/2006 | Lopez et al. ................... | 433/224 |
| 7,163,401 B2 * | 1/2007 | Karmaker et al. ............. | 433/224 |
| 7,168,952 B2 * | 1/2007 | Karmaker et al. ............. | 433/224 |
| 7,204,874 B2 * | 4/2007 | Jia et al. ........................ | 106/35 |
| 7,204,875 B2 * | 4/2007 | Jia et al. ........................ | 106/35 |
| 7,211,136 B2 * | 5/2007 | Jia et al. ........................ | 106/35 |
| 7,303,817 B2 * | 12/2007 | Jia ................................. | 428/375 |
| 7,462,650 B2 * | 12/2008 | Sommerlade et al. .......... | 522/36 |
| 2002/0051952 A1 * | 5/2002 | Kamohara et al. ......... | 433/228.1 |
| 2002/0088372 A1 * | 7/2002 | Abiru et al. ..................... | 106/35 |
| 2006/0270748 A1 * | 11/2006 | Sommerlade et al. ............ | 522/6 |

FOREIGN PATENT DOCUMENTS

| | | | |
|---|---|---|---|
| GB | 2346617 A * | 8/2000 | |
| GB | 2353286 A * | 2/2001 | |
| GB | 2 368 341 A | 5/2002 | |
| JP | 11-228328 | 8/1999 | |
| JP | 2002-80318 | 3/2002 | |

OTHER PUBLICATIONS

Properties of Parafin Waxes, Turner, W. et. al. Industrial and Engineering Chemistry, vol. 47, No. 6, Jun. 1955, 1219-1226.*
Extended Search Report issued Nov. 29, 2010 in Europe Application No. 09011821.7.

* cited by examiner

*Primary Examiner* — James J Seidleck
*Assistant Examiner* — Peter A Salamon
(74) *Attorney, Agent, or Firm* — Oblon, Spivak, McClelland, Maier & Neustadt, L.L.P.

(57) ABSTRACT

To provide a dental root canal-filling composition which is generally formed in a point shape, has high strength, is properly deformed so as to afford easy operativity for filling in a root canal, has improved wetting and adhering properties with a root canal-filling sealer and is less deteriorated by sterilization or chemical disinfection, the dental root canal-filling composition comprises one or more kinds of polyolefin resins selected from the group of polyethylene, polypropylene, and a copolymer of polyethylene and polypropylene, a styrene block copolymer, one or more kinds of thermoplastic resins selected from the group of ester gum, rosin, an alicyclic saturated hydrocarbon resin, a terpene resin, and an aliphatic petroleum resin, and one or more kinds of inorganic fillers selected from the group of zinc oxide, barium sulfate, zirconium oxide, titanium oxide, ytterbium fluoride, a barium glass, and an aluminosilicate glass.

6 Claims, No Drawings

DENTAL ROOT CANAL-FILLING COMPOSITION

BACKGROUND OF THE INVENTION

1. Field of the Invention

The present invention relates to a dental root canal-filling composition used in a dental root canal treatment.

2. Description of the Conventional Art

As for treatments of a pulp disease and a periapical periodontal disease in a dental treatment, a root canal treatment is widely used. In the root canal treatment, a point-shaped and stable material is filled in a root canal after a dental pulp extraction so as to seal a void in the root canal, and thus infection routes between the root canal and a periodontal tissue and between the root canal and an oral cavity are blocked. The material is filled in a root canal after removal of a pulp polluted with bacteria in the root canal, cleaning, sterilization, and formation of the root canal at the time of the root canal treatment. This composition is a dental filling materials for root canal. A dental filling materials for root canal most widely used now is a thin needle-shaped filling materials for root canal called a gutta-percha point mainly including gutta-percha (natural transpolyisoprene) and zinc oxide, and the filling materials for root canal is filled in a root canal after a dental pulp extraction. However, there is a problem that the dental filling materials for root canal mainly including gutta-percha is easily deteriorated due to sterilization and chemical disinfection.

A conventionally used dental filling materials for root canal mainly including gutta-percha is not sufficiently deformed in a root canal due to lack of proper flexibility, and thus it is very hard to carry out a filling operation. As a result of this, a filling ratio of the dental filling materials for root canal in the root canal decreases and voids are created, so that a later lesion may be caused. Thus, the present applicant previously filed a patent application for a dental root canal-filling composition, which has high strength, is not broken easily, and is properly deformed so as to afford an easy operativity for filling in a root canal, as in Japanese Patent Application Laid-Open No. 2002-80318.

However, since the dental root canal-filling composition also mainly includes gutta-percha, and thus there is a problem that the composition is easily deteriorated due to sterilization or chemical disinfection. Further, the conventional dental filling materials for root canal does not have sufficient wetting and adhering properties with a paste material called a root canal-filling sealer, which is used for improving adhesion between a root canal wall and the dental filling materials for root canal inserted into the root canal. If the wetting and adhering properties between the dental filling materials for root canal and the root canal-filling sealer is insufficient, the adhesion between the dental filling materials for root canal and the root canal-filling sealer is insufficient. As a result, since a sealing property of the root canal is insufficient, a lesion may be caused.

SUMMARY OF THE INVENTION

Problem to be Solved by the Invention

The present invention is directed to provide a dental root canal-filling composition generally formed in a point shape to be provided. The dental root canal-filling composition has high strength, is not broken easily, and is properly deformed so as to afford an easy operativity for filling in a root canal. Further, the dental root canal-filling composition has more excellent wetting and adhering properties with a root canal-filling sealer than those of a conventional filling materials for root canal currently used for a root canal treatment, and is less deteriorated by sterilization or chemical disinfection.

Means for Solving the Problem

Present inventors carried out earnest works to solve the aforementioned problems and, as a result, they found out the followings to complete the present invention. A dental root canal-filling composition, which consists of one or more kinds of polyolefin resins selected from the group of polyethylene, polypropylene, and a copolymer of polyethylene and polypropylene, a styrene block copolymer, one or more kinds of thermoplastic resins selected from the group of ester gum, rosin, an alicyclic saturated hydrocarbon resin, a terpene resin, and an aliphatic petroleum resin, and one or more kinds of inorganic fillers selected from the group of zinc oxide, barium sulfate, zirconium oxide, titanium oxide, ytterbium fluoride, a barium glass, and an aluminosilicate glass, has extremely proper filling property in a root canal, has excellent wetting property with a root canal-filling sealer, and is less deteriorated by sterilization or chemical disinfection.

That is, the present invention is a dental root canal-filling composition comprising (A) 1 to 40% by weight of one or more kinds of polyolefin resins selected from the group of polyethylene, polypropylene, and a copolymer of polyethylene and polypropylene, (B) 1 to 60% by weight of a styrene block copolymer, (C) 0.1 to 20% by weight of one or more kinds of thermoplastic resins selected from the group of ester gum, rosin, an alicyclic saturated hydrocarbon resin, a terpene resin, and an aliphatic petroleum resin, and (D) 30 to 95% by weight of one or more kinds of inorganic fillers selected from the group of zinc oxide, barium sulfate, zirconium oxide, titanium oxide, ytterbium fluoride, a barium glass, and an aluminosilicate glass.

Effect of the Invention

The dental root canal-filling composition according to the present invention has high strength, is not broken easily, and is properly deformed so as to afford an easy operativity for filling in a root canal. Further, the dental root canal-filling composition has more excellent wetting and adhering properties with a root canal-filling sealer, has very proper filling property in a root canal, and is less deteriorated by sterilization or chemical disinfection. The dental root canal-filling composition according to the present invention can improve each property required for traditional dental filling materials for root canal.

DETAILED DESCRIPTION OF PREFERRED EMBODIMENT

The (A) component is one or more kinds of polyolefin resins selected from the group of polyethylene, polypropylene, and a copolymer of polyethylene and polypropylene, and is a component for giving basic strength and formability as a dental filling materials for root canal. Transpolyisoprene which is a main component of gutta-percha as a natural resin may be deteriorated by carrying out sterilization or chemical disinfection. However, the dental root canal-filling composition according to the present invention does not include the transpolyisoprene, so that the composition is hardly deteriorated by subjecting it to sterilization or chemical disinfection.

Further, polyethylene, polypropylene, and a copolymer of polyethylene and polypropylene are resins generally used for a film or various kinds of formed products. These resins are generally hard, and hardly show rubbery elasticity. However, by combining the resin with (B) and (C) components described below, proper flexibility, plasticity, and filling property which are necessary for the dental root canal-filling composition can be given.

The content of the (A) component is necessarily 1 to 40% by weight. If the content is less than 1% by weight, the strength necessary for the dental root canal-filling composition cannot be given, and a filling operation in a root canal becomes difficult. If the content is more than 40% by weight, the blending amount of an inorganic filler as the (D) component described below becomes small, so that X-ray imaging performance decreases so as to make confirmation by an X-ray difficult. As for polyethylene, high-density polyethylene, low-density polyethylene, and linear low-density polyethylene can be used.

A styrene block copolymer as the (B) component has elasticity, so that, by the copolymer being used with the (A) component, proper flexibility can be given to the dental root canal-filling composition, the composition is hardly broken during a filling operation, and a sealing property between the dental filling materials for root canal themselves or the dental filling materials for root canal and a root canal wall can be improved when being pressed and contacted. For examples of a styrene block copolymer, a block copolymer of polystyrene and polybutadiene, a block copolymer of polystyrene and polyisoprene, and a block copolymer of polystyrene and polyolefin can be used.

The blending amount of the (B) component is necessarily 1 to 60% by weight. If the amount is less than 1% by weight, the dental filling materials for root canal becomes too hard, and thus is broken easily during a filling operation, and the dental filling materials for root canal can hardly reach an apical area. If the amount is more than 60% by weight, the dental filling materials for root canal becomes too soft, so it hardly reaches the apical area. In addition, the blending amount of an inorganic filler as the (D) component becomes small, so that X-ray imaging performance decreases so as to make confirmation by an X-ray difficult.

The (C) component is one or more kinds of thermoplastic resins selected from the group of ester gum, rosin, an alicyclic saturated hydrocarbon resin, a terpene resin, and an aliphatic petroleum resin. This component is for giving the typical properties of the dental root canal-filling composition according to the present invention, that is, for improving sealing property by increasing wetting and adhering properties to a dental filling sealer. Further, this component is effective for giving proper plasticity to the dental root canal-filling composition so as to make a filling operation easy. The blending amount of the (C) component is 0.1 to 20% by weight. If the amount is less than 0.1% by weight, an effect for giving wetting and adhering properties to the dental filling sealer of the dental root canal-filling composition is not sufficient, and plasticity decreases, so that a filling operation becomes difficult. If the amount is more than 20% by weight, the strength of the dental canal root-filling composition itself decreases, so that a filling operation in a root canal becomes difficult.

The ester gum can be generally acquired by esterifying rosin with glycerin, and also can be acquired by esterifying rosin with polyhydric alcohol or esterifying hydrogenated rosin with glycerin. As for the rosin, gum rosin, wood rosin and tall oil rosin can be used. Further, a number average molecular weight of a general alicyclic saturated hydrocarbon resin is 500 to 900, but is preferably 550 to 750 in order to easily soften the composition as the dental root canal-filling composition. As for the terpene resin, there is a terpene resin added with hydrogen in addition to a general terpene resin. The terpene resin added with hydrogen can be also used and a number average molecular weight of the terpene resin added with hydrogen is preferably 400 to 800. As for the aliphatic petroleum resin, a number average molecular weight is preferably 700 to 1200.

The (D) component is one or more kinds of inorganic fillers selected from the group of zinc oxide, barium sulfate, zirconium oxide, titanium oxide, ytterbium fluoride, a barium glass, and an aluminosilicate glass, and can give strength and an X-ray imaging performance to the dental filling materials for root canal. The content is from 30 to 95% by weight. If the content is less than 30% by weight, the strength of the composition becomes low and the X-ray imaging performance is also insufficient. If the content is more than 95% by weight, the composition becomes fragile and viscosity at the time of production is too high, so that the productivity of the dental root canal-filling composition decreases.

In addition, in the dental root canal-filling composition according to the present invention, various kinds of inorganic or organic coloring agents, antibacterial agents, and plasticizers used for a conventional root canal-filling composition can be used within a range not losing the properties according to necessity.

[Examples]

The present invention will be described in detail below with examples, but the present invention is not limited to these examples.

Dental root canal-filling compositions used for each example and comparative example were produced by weighing each component according to a blending ratio shown in Table 1, and heating (130 to 170° C.) and mixing these components under a specific heating condition by a pressurizing kneader. These dental root canal-filling compositions were formed in a sheet shape having a thickness of 2 mm. In addition, as for comparative example 3, a sheet-shaped composition was produced using a conventional dental filling materials for root canal (a product name: GC GUTTA-PERCHA POINT, produced by GC Corporation).

[Wetting Property Test]

A specimen having length of 10 mm, width of 10 mm, and thickness of 2 mm was produced in order to evaluate wetting property of the dental root canal-filling composition to the root canal filling sealer. Then, about 0.3 g of a liquid component of a root canal filling sealer (a product name: CANALS, produced by Showa Yakuhin KaKo Co., Ltd.) mainly including eugenol was dropped onto a center part of the specimen. After elapsing 10 seconds, the expanding degree of the liquid was evaluated with the following standards.

○: The liquid spreaded largely, so that wetting property was high.

Δ: The liquid spreaded very little.

x: The liquid did not spread but remained in a ball shape, so that wetting property was low.

[Evaluation of Adhering Property]

In order to evaluate adhering property to the root canal filling sealer, a specimen having length of 10 mm, width of 10 mm, and thickness of 2 mm was placed on a center part of a silicone mold having a hole with 25 mm diameter, and embedded with a dental ordinary self-curing acrylic resin (a product name: GC UNIFAST III, produced by GC Corporation). The surface was prepared with a wet 1000-grit silicon carbide paper, and water content on the surface was removed. Then, a seal having a hole with 3 mm diameter was bonded to the surface. A silicone mold having a diameter of 4 mm and thickness of 2 mm was placed so as to expose a specified surface, and a root canal filling sealer mainly including zinc oxide and eugenol (a product name: CANALS, produced by Showa Yakuhin Kako Co., Ltd.) was filled into the mold. The specimen was kept at 37° C. and humidity of 100% for 24 hours, and the specimen was subjected to a shear bond strength test at a crosshead speed of 1 mm/min with a universal testing machine (a product name: Autograph AG-IS, produced by Shimadzu Corporation). Then, the interface between the test body and the root canal filling sealer was confirmed. As a result, when the dental root canal-filling composition was sufficiently bonded to the root canal filling sealer and either of the dental root canal-filling composition or the root canal filling sealer was broken to be separated, this state was evaluated as "○". When the dental root canal-filling composition was not sufficiently bonded to the root canal filling sealer and the both were completely separated at the adhesion surface, this state was evaluated as "x".

[Evaluation to Sterilization or Chemical Disinfection]

In order to make evaluation with respect to sterilization or chemical disinfection, a change of the dental root canal-filling composition shown in each example and comparative example after and before EOG sterilization was evaluated. As for the evaluation, the composition of each example and comparative example was formed into a point shape (#40 type), and breaking states and bending states before and after EOG sterilization were compared by pressing its top end to the inside surface of a finger to bend the composition. When the breaking states and bending states did not change before and after the sterilization, this state was evaluated as "○", and the case other than this state were evaluated as "x".

[Evaluation of Easiness of Filling]

In order to evaluate easiness of filling into a root canal, easiness when filling a dental root canal-filling composition of each example and comparative examples into a root canal model (a product name: Dental Root Canal Model, produced by Nissin Dental Products Inc. was evaluated). The evaluation was carried out by a lateral condensation of root canal filling method using a spreader. As for the evaluation, a point-shaped (#40 type) composition was pushed in by the spreader. When the composition was filled easily, this state was evaluated as "○", and when the point-shaped composition was almost not deformed even using the spreader so that filling was very hard, this state was evaluated as "x".

TABLE 1

| Components | Materials | Example 1 | Example 2 | Example 3 | Example 4 | Comparative example 1 | Comparative example 2 | Comparative example 3 |
|---|---|---|---|---|---|---|---|---|
| One or more kinds of polyolefin resins selected from the group of polyethylene, polypropylene, and a copolymer of polyethylene and polypropylene | Polyethylene | | | 3 | | | | GC GUTTA-PERCHA POINT |
| | Polypropylene | | 4 | | 12 | | 30 | |
| | Copolymer of polyethylene and polypropylene | 8 | | | 20 | | | |
| Resin other than above | Transpolyisoprene | | | | | 15 | | |
| Styrene block copolymer | Block copolymer of polystyrene and ethylene/propylene copolymer | 51 | | | | | | |
| | Block copolymer of polystyrene and polyisoprene | | 16 | | 10 | | 6 | |
| | Block copolymer of polystyrene and polybutadiene | | | 4 | | | | |
| One or more kinds of thermoplastic resins selected from the group of ester gum, rosin, an alicyclic saturated hydrocarbon resin, a terpene resin, and an aliphatic petroleum resin | Ester gum | | 2 | | 10 | | | |
| | Rosin | 0.4 | | | | | | |
| | Terpene resin | | | | 5 | | | |
| | Alicyclic saturated hydrocarbon resin (having an average molecular weight of 570) | | | 3 | | | | |
| Thermoplastic resins other than above | Paraffin wax | | | | | | 4 | |
| Inorganic filler | Zinc oxide | | 78 | 25 | 23 | 85 | 60 | |
| | Barium sulfate | 40.6 | | | 20 | | | |
| | Zirconium oxide | | | 65 | | | | |
| Other | Red oxide (coloring agent) | | | | 1 | | | |
| | Total | 100 | 100 | 100 | 100 | 100 | 100 | |
| | Wetting property test | ○ | ○ | ○ | ○ | Δ | X | Δ |
| | Evaluation of adhering property | ○ | ○ | ○ | ○ | X | X | X |
| | Evaluation to sterilization or chemical disinfection | ○ | ○ | ○ | ○ | X | ○ | X |
| | Evaluation of easiness of filling | ○ | ○ | ○ | ○ | X | ○ | X |

Clearly from Table 1, it was confirmed that the dental root canal filling compositions according to the present invention shown in the examples had more excellent wetting and adhering properties to the root canal filling sealer than those of the comparative examples 1, 2 and 3. Further, it was confirmed that the compositions of the comparative examples tend to be broken easily because they became fragile due to deterioration. By contrast, it was confirmed that the dental root canal filling compositions according to the present invention shown in the examples did not change before and after EOG sterilization, and had less deterioration due to sterilization or chemical disinfection.

What is claimed is:
1. A dental root canal-filling composition comprising:
   A) 1 to 40% by weight of one or more kinds of polyolefin resins selected from the group consisting of polyethylene, polypropylene, and a copolymer of polyethylene and polypropylene;

B) 1 to 60% by weight of a styrene block copolymer;
C) 0.1 to 20% by weight of one or more kinds of thermoplastic resins selected from the group consisting of ester gum, rosin, an alicyclic saturated hydrocarbon resin having a number average molecular weight of 550 to 750, a terpene resin, and an aliphatic petroleum resin having a number average molecular weight of 700 to 1200; and
D) 30 to 95% by weight of one or more kinds of inorganic fillers selected from the group consisting of zinc oxide, barium sulfate, zirconium oxide, titanium oxide, ytterbium fluoride, a barium glass, and an aluminosilicate glass.

2. The dental root canal-filling composition according to claim 1, wherein trans-polyisoprene is not present.

3. The dental root canal-filling composition according to claim 1, wherein the styrene block copolymer is at least one selected from the group consisting of a block copolymer of polystyrene and polybutadiene, a block copolymer of polystyrene and polyisoprene, and a block copolymer of polystyrene and polyolefin.

4. The dental root canal-filling composition according to claim 1, wherein the one or more thermoplastic resin is an ester gum obtained by esterifying rosin with glycerin, by esterifying rosin with a polyhydric alcohol or esterifying hydrogenated rosin with glycerin.

5. The dental root canal-filling composition according to claim 1, wherein the one or more thermoplastic resin is selected from the group consisting of rosin, gum rosin, wood rosin and tall oil rosin.

6. The dental root canal-filling composition according to claim 1, wherein the one or more thermoplastic resin is a terpene resin, a hydrogenated terpene resin or a mixture thereof.

* * * * *